United States Patent [19]

Frazee et al.

[11] 3,957,985

[45] May 18, 1976

[54] MANDELAMIDOCEPHALOSPORINS WITH IMPROVED PROPERTIES

[75] Inventors: James S. Frazee, Collingswood, N.J.; Timothy Yu-Wen Jen, Broomall, Pa.

[73] Assignee: SmithKline Corporation, Philadelphia, Pa.

[22] Filed: Feb. 25, 1975

[21] Appl. No.: 552,908

Related U.S. Application Data

[62] Division of Ser. No. 376,653, July 5, 1973, Pat. No. 3,884,914.

[52] U.S. Cl. ............................................. 424/246
[51] Int. Cl.$^2$ .................................. A61K 31/54

[58] Field of Search ................. 424/246; 260/243 C

[56] References Cited
UNITED STATES PATENTS

| | | | |
|---|---|---|---|
| 3,516,997 | 6/1970 | Takano et al. | 260/243 C |
| 3,641,021 | 2/1972 | Ryan | 260/243 C |

*Primary Examiner*—Jerome D. Goldberg
*Attorney, Agent, or Firm*—Stuart R. Suter; Alan D. Lourie; William H. Edgerton

[57] ABSTRACT

7-Mandelamido-3-(1-oxidopyridylthiomethyl)-3-cephem-4-carboxylic acid and substituted derivatives which have antibacterial activity are disclosed.

10 Claims, No Drawings

MANDELAMIDOCEPHALOSPORINS WITH IMPROVED PROPERTIES

This is a division of application Ser. No. 376,653 filed July 5, 1973, now U.S. Pat. No. 3,884,914.

This invention relates to cephalosporin compounds having 1-oxidopyridylthiomethyl and mandelamido groups at positions 3 and 7, respectively. The compounds are broad spectrum antibacterials.

Various unsubstituted or substituted mandelamido cephalosporins have been reported. 7-Mandelamidocephalosporanic acid is disclosed in U.S. Pat. No. 3,167,549 along with mono or disubstituted derivatives. In U.S. Pat. No. 3,641,021 unsubstituted or monosubstituted mandelamidocephalosporins with a thiadiazoylthiomethyl or a tetrazolylthiomethyl group at position 3 are reported. Cephalosporins with a pyridylthiomethyl-N-oxide group at position 3 are described in Belgian Patents 762725, 770804, and 777260 and Japanese Patent 4717793. For example, 7-(α-aminophenylacetamido)-3-(1-oxide-2-pyridylthiomethyl)-3-cephem-4-carboxylic acid and other 7-acylamido derivatives are reported in Belgian Patent 770804.

The compounds of this invention are represented by the formula

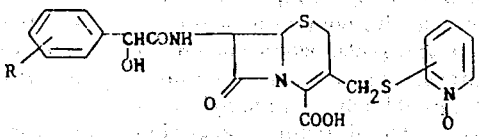

where R is hydrogen, alkyl of $C_1$–$C_4$, alkoxy of $C_1$–$C_4$, fluoro, chloro, bromo, hydroxy, amino, nitro, or trifluoromethyl.

Preferred compounds are those where R is p-hydroxy, m-amino, m-trifluoromethyl, m-nitro, m-chloro, p-methyl, or hydrogen. Also preferred are the compounds where the pyridyl moiety is bonded at the 2 position on the pyridine ring. Particularly preferred are the compounds where R is hydrogen.

Pharmaceutically acceptable salts of the compounds are also within the scope of the invention. Bases which form pharmaceutically acceptable salts with acids are well known to those skilled in the art. For example, common cations include sodium, potassium, and ammonium.

The compounds are prepared by the reaction of a mandelamidocephalosporanic acid with a mercaptopyridine-N-oxide or a salt thereof. The 3-acetoxy group is displaced by the mercapto compound to give the compounds of the invention. Alternatively the compounds are prepared by displacement of the 3-acetoxy of 7-aminocephalosporanic acid (7-ACA) with the above mercapto compound and then acylation with the desired mandelic acid. During the acylation reaction, the hydroxy group of the mandelic acid must be protected with a protecting group, many of which are known in the art. For example, the tetrahydropyranyl ether or the formate, dichloroacetate, or other ester may be used. Standard methods are used to remove the protecting groups after the acylation reaction is completed.

The carboxylic acid is activated prior to the acylation reaction by standard methods, such as the acid chloride, mixed anhydride or activated ester. All the above procedures are well-known reactions, the choice of exact methods and conditions being within the ability of one skilled in the art and not critical to our invention.

Due to the asymmetric carbon in the mandelic acid side chain optical isomers exist. The diasteromers having the D configuration are preferred; however, those having the L configuration and the racemic mixtures are within the scope of the invention.

The compounds have broad spectrum antibacterial activity. In vitro tests indicate the compounds to have activity against both Gram-positive and Gram-negative organisms. Studies in mice showed protection against E. coli and Klebsiella pneumoniae infections. For example, 7-mandelamido-3-(1-oxido-2-pyridylthiomethyl)-3-cephem-4-carboxylic acid gave an $ED_{50}$ of 9.4 and 3 mg/kg against E. coli and K. pneumoniae, respectively, when administered subcutaneously to infected mice.

The compounds are formulated as other cephalosporins by standard methods which are well known in the art. Daily dosages range from 1-8 grams depending on the subject and infection being treated. These total daily dosages are usually divided and administered at regular intervals.

The following examples are given to illustrate the invention and are not to be considered limitative.

EXAMPLE 1

7-(D-Mandelamido)-3-(1-oxido-2-pyridylthiomethyl)-3-cephem-4-carboxylic acid.

A solution of 7-(D-mandelamido)cephalosporanic acid, methanolate (2.41 g, 5 mmol) and $NaHCO_3$ (420 mg, 5 mmol) in $H_2O$ (30 ml) was treated with a solution of sodium-2-mercaptopyridine-N-oxide (900 mg, 6 mmol) in $H_2O$ (5 ml). After 24 hours at 58°, the reaction was cooled, diluted with acetone (30 ml), and acidified with 3N HCl to pH 1. The acidic solution was concentrated until crystallization began, and then chilled. The crystalline product was filtered, washed with acetone and ether and dried; 1.6 g (68%), mp 216° (dec.).

EXAMPLE 2

When 7-(4-methylmandelamido)cephalosporanic acid, 7-(4-hydroxymandelamido)cephalosporanic acid, 7-(4-methoxymandelamido)cephalosporanic acid, 7-(3-nitromandelamido)cephalosporanic acid, 7-(3-chloromandelamido) cephalosporanic acid, 7-(3-aminomandelamido)cephalosporanic acid or 7-(3-trifluoromethylmandelamido)cephalosporanic acid is substituted for mandelamidocephalosporanic acid in Example 1 the following compounds are obtained.

7-(4-methylmandelamido)-3-(1-oxido-2-pyridylthiomethyl)-3-cephem-4-carboxylic acid 7-(4-hydroxymandelamido)-3-(1-oxido-2-pyridylthiomethyl)-3-cephem-4-carboxylic acid 7-(4-methoxymandelamido)-3-(1-oxido-2-pyridylthiomethyl)-3-cephem-4-carboxylic acid 7-(3-nitromandelamido)-3-(1-oxido-2-pyridylthiomethyl)-3-cephem-4-carboxylic acid 7-(3-chloromandelamido)-3-(1-oxido-2-pyridylthiomethyl)-3-cephem-4-carboxylic acid 7-(3-aminomandelamido)-3-(1-oxido-2-pyridylthiomethyl)-3-cephem-4-carboxylic acid 7-(3-trifluoromethylmandelamido)-3-(1-oxido-2-pyridylthiomethyl)-3-cephem-4-carboxylic acid

EXAMPLE 3

When sodium-4-mercaptopyridine-N-oxide is substituted for sodium-2-mercaptopyridine-N-oxide in Examples 1 and 2 the corresponding 3-(1-oxido-4-pyridylthiomethyl)cephalosporins are obtained.

EXAMPLE 4

An injectable pharmaceutical composition is prepared by dissolution of sodium 7-mandelamido-3-(1-oxido-2-pyridylthiomethyl)-3-cephem-4-carboxylate (0.25–1.0 g) in sterile water or normal saline solution (1–2 ml). Pharmaceutical compositions of the other compounds of this invention are prepared in the same manner.

We claim:

1. A pharmaceutical composition comprising an antibacterially effective amount of a compound of the formula

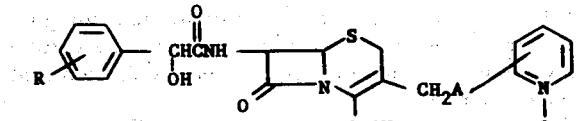

where
R is hydrogen, alkyl or alkoxy of $C_1$–$C_4$, fluoro, chloro, bromo, hydroxy, amino, nitro, or trifluoromethyl or a non-toxic pharmaceutically acceptable salt thereof, and a pharmaceutically acceptable carrier therefor.

2. A pharmaceutical composition comprising an antibacterially effective amount of a compound as claimed in claim 1 where R is hydrogen, p-hydroxy, m-amino, m-trifluoromethyl, m-nitro, m-chloro, p-methoxy or p-methyl and a pharmaceutically acceptable carrier therefor.

3. A pharmaceutical composition comprising an antibacterially effective amount of a compound as claimed in claim 2 where the sulfur is bonded to position 2 of the pyridine ring and a pharmaceutically acceptable carrier therefor.

4. A pharmaceutical composition comprising an antibacterially effective amount of a compound as claimed in claim 3 being the compound 7-mandelamido-3-(1-oxido-2-pyridylthiomethyl)-3-cephem-4-carboxylic acid and a pharmaceutically acceptable carrier therefor.

5. A pharmaceutical composition comprising an antibacterially effective amount of a compound as claimed in claim 3 being the compound 7-(4-hydroxymandelamido)-3-(1-oxido-2-pyridylthiomethyl)-3-cephem-4-carboxylic acid and a pharmaceutically acceptable carrier therefor.

6. A method of treating bacterial infections comprising administering by injection to a warm-blooded animal an effective but non-toxic dose of 250–1000 mg of a compound of the formula

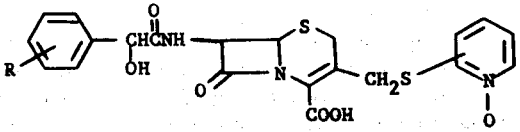

where
R is hydrogen, alkyl or alkoxy of $C_1$–$C_4$, fluoro, chloro, bromo, hydroxy, amino, nitro, or trifluoromethyl or a non-toxic pharmaceutically acceptable salt thereof, and a pharmaceutically acceptable salt thereof.

7. A method of treating bacterial infections comprising administering by injection to a warm-blooded animal an effective but non-toxic dose of 250–1000 mg of a compound as claimed in claim 6 where R is hydrogen, p-hydroxy, m-amino, m-trifluoromethyl, m-nitro, m-chloro, p-methoxy or p-methyl.

8. A method of treating bacterial infections comprising administering by injection to a warm-blooded animal an effective but non-toxic dose of 250–1000 mg of a compound as claimed in claim 7 where the sulfur is bonded to position 2 of the pyridine ring.

9. A method of treating bacterial infections comprising administering by injection to a warm-blooded animal an effective but non-toxic dose of 250–1000 mg of a compound as claimed in claim 8 being the compound 7-mandelamido-3-(1-oxido-2-pyridylthiomethyl)-3-cephem-4-carboxylic acid.

10. A method of treating bacterial infections comprising administering by injection to a warm-blooded animal an effective but non-toxic dose of 250–1000 mg of a compound as claimed in claim 8 being the compound 7-(4-hydroxymandelamido)-3-(1-oxido-2-pyridylthiomethyl)-3-cephem-4-carboxylic acid.

* * * * *